United States Patent [19]

Maggio

[11] Patent Number: 4,715,374

[45] Date of Patent: Dec. 29, 1987

[54] DISPOSABLE AUTOMATIC LANCET

[75] Inventor: Joseph Maggio, Hialeah, Fla.

[73] Assignee: Medicore, Inc., Hialeah, Fla.

[21] Appl. No.: 930,515

[22] Filed: Nov. 14, 1986

[51] Int. Cl.$^4$ ............................................. A61B 17/32
[52] U.S. Cl. ................................... 128/314; 128/329 R
[58] Field of Search ................... 128/314, 315, 329 R; 604/156, 157, 134–137, 110; 30/366, 367, 155

[56] References Cited

U.S. PATENT DOCUMENTS

| | | | |
|---|---|---|---|
| 2,183,482 | 12/1939 | Kurkjian | 604/135 |
| 3,320,954 | 5/1967 | Cowley | 604/110 |
| 3,760,809 | 9/1973 | Campbell, Jr. | 128/314 |
| 4,230,118 | 10/1980 | Holman | 128/314 |
| 4,539,988 | 9/1985 | Shirley et al. | 128/314 |
| 4,658,821 | 4/1987 | Chiodo et al. | 128/314 |

Primary Examiner—Dalton L. Truluck
Assistant Examiner—F. Wilkens
Attorney, Agent, or Firm—Oltman and Flynn

[57] ABSTRACT

A disposable automatic lancet which can be used only once. A lancet blade is on a spring arm in a housing, and the spring arm is cocked just before the lancing procedure by pulling a flexible line extending through an opening in the housing. After cocking, the pull line may be broken off so that it cannot be pulled again, thus limiting the lancet to use only once.

4 Claims, 9 Drawing Figures

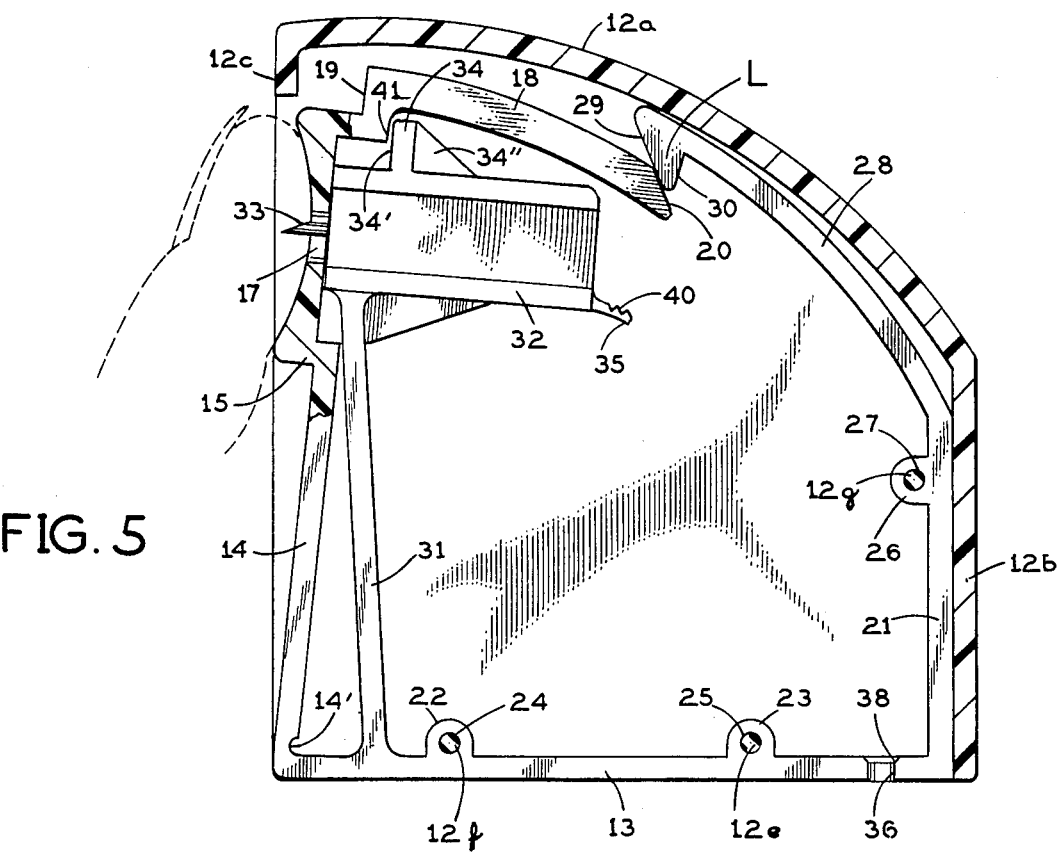
FIG. 5
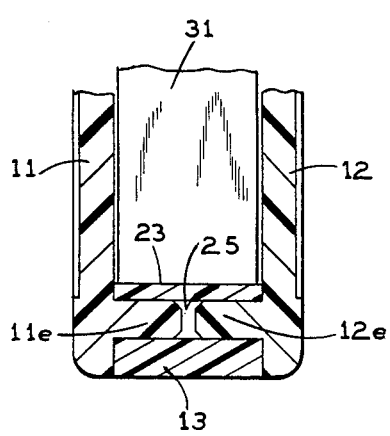
FIG. 6
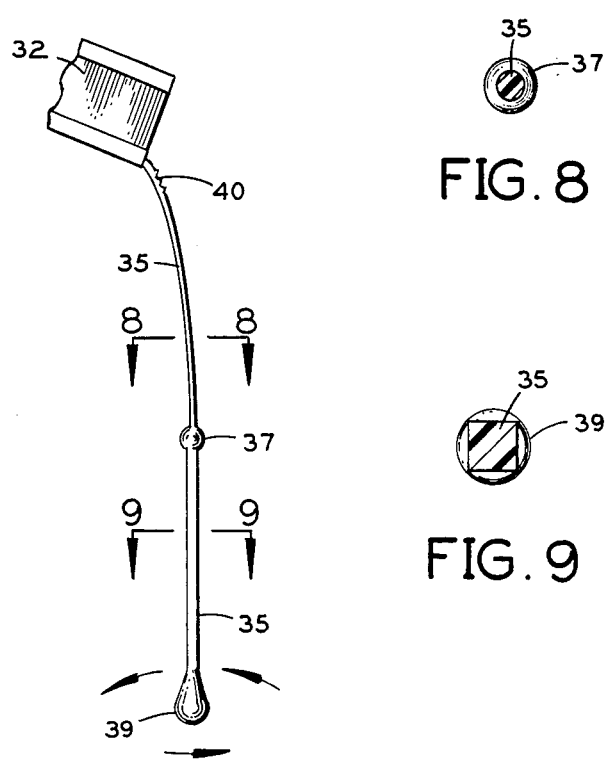
FIG. 7
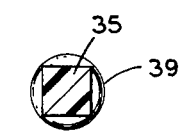
FIG. 8
FIG. 9

DISPOSABLE AUTOMATIC LANCET

SUMMARY OF THE INVENTION

This invention relates to a disposable automatic surgical lancet.

In the use of surgical lancets it is desirable to minimize any apprehension the patient may have about the procedure, as well as to make the procedure itself as safe and comfortable as possible. In accordance with the present invention, these objectives are achieved by enclosing the lancet blade in a housing having a seat for the patient's finger tip which is located on the outside of the housing. The lancet blade is on a spring arm which need not be cocked in its retracted, stressed position until just before the lancing procedure is to take place, thereby reducing the possibility of accidental release of the spring arm from the cocked position.

In accordance with one important aspect of the invention, the spring arm is cocked by exerting a pull on a flexible line extending through an opening in the housing. After the spring arm has been cocked, the pull line may be twisted, causing it to break at a weakened location inside the housing so that it cannot be used again to cock the spring arm another time, thus limiting the lancet to use only once.

Preferably, the spring arm is held in its cocked position by a cantilevered element which releases the cocked spring arm when the patient's finger pushes, or is pushed, against its seat on the housing.

Preferably, the present lancet has a central frame which forms the front and bottom of the housing, and opposite side pieces attached to the central frame and providing the sides, top and back of the housing. The spring arm is formed integral with the frame, extending up from the bottom of the frame and carrying a lancet blade holder on its free upper end. The frame presents a cantilevered rear top element with a downwardly-projecting, rearwardly-facing shoulder at its free front end to engage the lancet blade holder for keeping the spring arm cocked. The frame also presents a cantilevered front top element with a free back end for displacing the front end of the rear top element upward to release the lancet blade holder when this front top element is displaced rearward by a push on the patient's finger.

A principal object of this invention is to provide an automatic surgical lancet with a novel arrangement for limiting it to a single use.

Another object of this invention is to provide a novel automatic surgical lancet of extremely simple and economical construction.

Another object of this invention is to provide a novel surgical lancet which is constructed to minimize any discomfort or apprehension the patient may feel.

Another object of this invention is to provide a novel surgical lancet having a lancet blade on a spring arm which may be cocked in a stressed position and then released from that position so unobtrusively that the pricking of the patient's finger may be over before the patient realizes what is happening.

Another object of this invention is to provide a novel surgical lancet having a lancet blade on a spring arm which need not be cocked until just before the pricking operation is to take place.

Further objects and advantages of this invention will be apparent from the following detailed description of a presently preferred embodiment which is illustrated schematically in the accompanying drawings.

DESCRIPTION OF THE DRAWINGS

FIG. 5 is a view generally similar to FIG. 3 and showing the spring arm after it has been released and has carried the lancet blade or needle to its finger-penetrating position;
FIG. 6 is a fragmentary vertical cross-section taken along the line 6—6 in FIG. 3;
FIG. 7 is an elevational view of the pull line for retracting the spring arm;
FIG. 8 is a cross-section through this pull line, taken along the line 8—8 in FIG. 7;
and
FIG. 9 is a cross-section through another part of this pull line, taken along the line 9—9 in FIG. 7.

Before explaining the disclosed embodiment of the present invention in detail, it is to be understood the invention is not limited in its application to the details of the particular arrangement shown, since the invention is capable of other embodiments. Also, the terminology used herein is for the purpose of description and not limitation.

DETAILED DESCRIPTION

Figure 1:
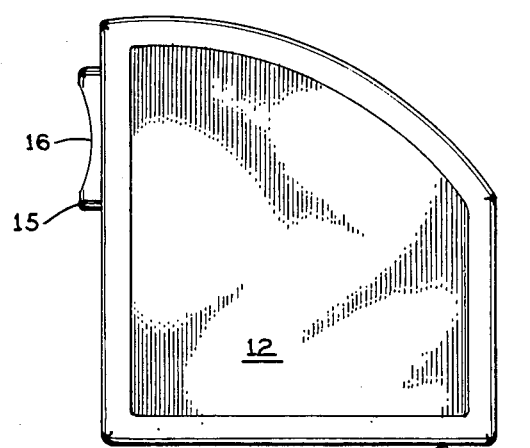
FIG. 1 is a side elevation of the present lancet.
Figure 2:
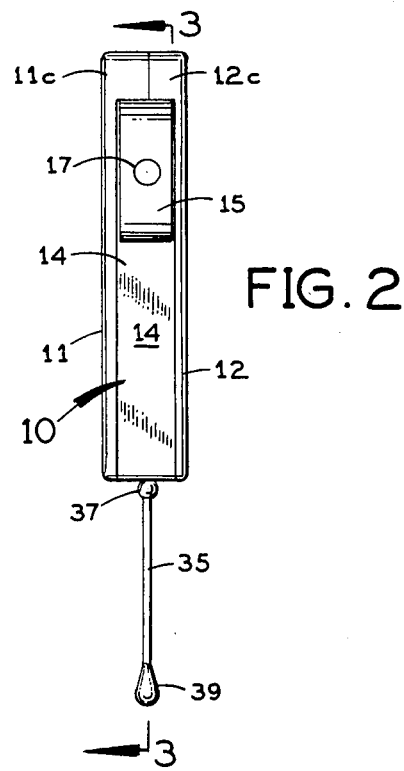
FIG. 2 is a front elevation.

Referring to FIG. 2, the present invention has a central frame 10 and opposite side pieces 11 and 12 which engage the frame 10 on opposite sides. The frame and the side pieces are molded of suitable plastic, such as propylene or nylon.

Figure 3:
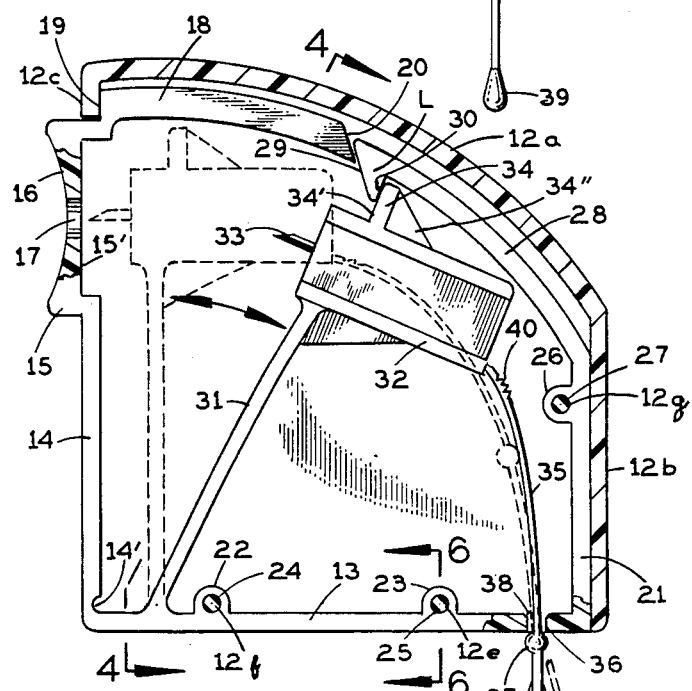
FIG. 3 is a vertical longitudinal section taken along the line 3—3 in FIG. 2.
Figure 4:
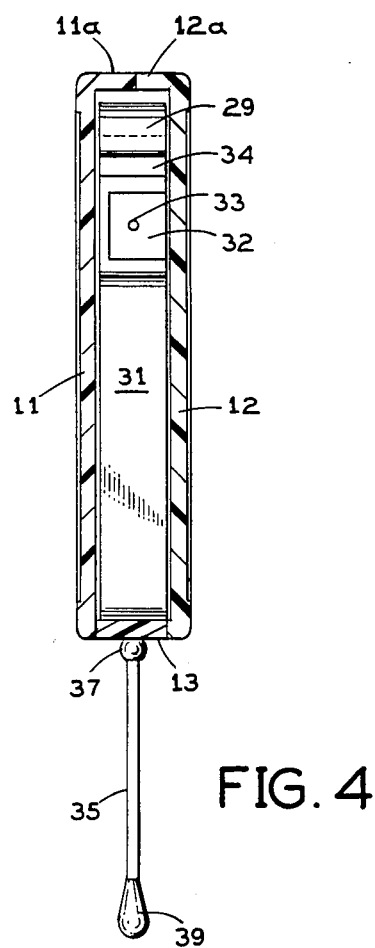
FIG. 4 is a vertical cross-section taken along the line 4—4 in FIG. 3 with the spring arm cocked.

As shown in FIG. 4, the side pieces at the top are formed with in-turned transverse flanges 11a and 12a which extend toward each other and abut against each other to form the rounded top wall of the housing of this lancet. As shown in FIG. 3, at its back end the top flange 12a on side piece 12 is joined to a downwardly extending, vertically elongated, in-turned flange 12b. The other side piece 11 has a similar in-turned, vertically elongated flange (not shown) which extends down from the back end of its curved top flange 11a and abuts against the inner edge of flange 12b to form the back wall of the lancet housing. At its front end the curved top flange 12a of side piece 12 is joined to a depending, short, vertical lip 12c (FIG. 3). The other side piece 11 has a similar lip 11c (FIG. 2) at the same location which abuts against lip 12c.

The central frame 10 presents a horizontally elongated, flat bottom segment 13 (FIGS. 3 and 4) and a flexible and resilient front segment 14 joined to the bottom segment 13 at the latter's front end and extending up from it. At the inside corner between segments 13 and 14 the material of the frame is of reduced thickness, as shown at 14' to facilitate the pivotal movement of the front segment 14 with respect to the bottom segment 13. A forwardly offset finger-receiving segment 15 at the upper end of the front segment of the frame presents a forwardly-facing concave depression 16 on which a person's finger can seat, as shown in FIG. 5. The finger-receiving segment 15 has a centrally located opening 17 for passing the lancet blade or needle, as explained hereinafter.

The depending, abutting, top front lips 11c and 12c of the side pieces and the upstanding front segment 14 and the finger-receiving segment 15 of the central frame together provide the front of the housing of the present lancet.

Above the finger-receiving segment 15 the central frame 10 presents a cantilevered, rearwardly extending, flexible and resilient, front top element 18 with a curvature parallel to that of the top flanges 12a and 11a of the side pieces 11 and 12. Where the front top element 18 is joined to the finger-receiving segment 15 the frame presents a forwardly-facing vertical shoulder 19 which normally engages the depending front lips 12c and 11c of the side pieces from behind, as shown in FIG. 3. At its rear end (to the right in FIG. 3) the front top element 18 of the frame presents a flat tapered face 20 which, in the upright position of the lancet shown in FIG. 3, is inclined downward and rearward at a small acute angle to the vertical.

The central frame 10 presents a vertically elongated back wall segment 21 extending up from the back end of its bottom wall segment 13. This back wall segment of the frame engages the inside faces of the rear flanges 12b and 11b of side pieces 12 and 11.

The bottom wall segment 13 of the frame presents a pair of upwardly projecting, rounded ears 22 and 23, formed with respective circular openings 24 and 25. As shown in FIG. 6, the opening 25 in ear 23 snugly receives short horizontal stems 11e and 12e on the inside of the side pieces 11 and 12, respectively. Similarly, the opening 24 in ear 22 snugly receives a short item 12f on side piece 12, as shown in FIG. 3, and a similar inwardly projecting stem (not shown) on the opposite side piece 11. Near its upper end the back segment 21 of the frame presents a forwardly projecting rounded ear 26 formed with a circular horizontal opening 27. The housing side piece 12 presents an inwardly projecting short horizontal stem 12g which is snugly received in this opening 27, as shown in FIG. 3. The other housing side piece 11 has a similar stem (not shown) which is also snugly received in the same opening. The snug engagement of these stems on the side pieces 11 and 12 in these openings in the ears 22, 23 and 26 on the central frame 10 holds the side pieces assembled to the central frame to form a unitary housing.

The central frame 10 presents a cantilevered, curved, rear top element 28 which extends forward and upward from the upper end of its upstanding back segment 21 generally parallel to the curved top flanges 12a and 11a on the side pieces. At its free front end the rear top element 28 of the frame presents a presents a depending lip L with a downwardly and rearwardly inclined front face 29, which extends close to and substantially parallel to the rear face 20 of the front top element 18 of the frame in the position of the parts shown in FIG. 3. Behind this front face this lip of the rear top element 28 of the frame presents a rearwardly facing transverse shoulder 30.

A flexible and resilient elongated spring arm 31 extends up from the bottom segment 13 of the frame a short distance in front of its front ear 22 and a short distance behind the upstanding front segment 14 of the frame. A holder 32 for a lancet blade or needle is joined to the spring arm 31 at the latter's upper end. The lancet blade or needle 33 projects forward from this holder, as shown in FIG. 3. The holder 32 presents an upwardly projecting extension 34 with a flat front face 34' lying in a plane which extends perpendicular to the longitudinal axis of the lancet blade 33. The top extension 34 on the holder presents a rearwardly and downwardly inclined back face 34" lying in a plane which extends at an acute angle to the longitudinal axis of the lancet blade 33.

A flexible pull line 35 extends rearward and downward from the holder 32, passing down through an opening 36 in the bottom segment 13 of the frame a short distance in front of the upstanding back segment 21 of the frame. This line is formed with a spherical bead 37 of a slightly larger diameter than that of the opening 36. This bead is located about midway along the length of the pull line. As shown in FIGS. 3 and 5, the opening 36 has a beveled top edge 38 which enables the bead 37 to be pulled down through this opening to cock the spring arm 31. The bottom edge of the opening 36 makes a sharp, right-angled corner of circular outline with the bottom face of the bottom segment 13 of the frame. The bead 37 on the pull line 35 engages this bottom corner of the opening 36 when the spring arm 31 is in its retracted, cocked position and the top extension 34 on the lancet blade holder 32 engages the shoulder 30 on the free front end of the cantilevered rear top element 28 of the frame.

Below this bead 37 the pull line has a lower extension which terminates in a rounded knob 39 which the user may grasp easily. As shown in FIG. 9, between the spherical bead 37 and the pull knob 39 on its lower end the pull line 35 has a solid rectangular cross-section. As shown in FIG. 8, above the bead 37 the pull line 35 has a solid circular cross-section smaller than its square cross-section below the bead. Close to its attachment to the back end of the blade or needle holder 32 the pull line 35 is formed with several closely spaced transverse grooves 40 to provide a weakened region of the pull line which will break first when the pull line is twisted.

The entire frame, comprising the bottom segment 13, the upstanding front segment 14, the finger-receiving segment 15, the cantilevered front top element 18, the upstanding back segment 21, and the cantilevered rear top element 28, the upstanding spring arm 31, the lancet blade holder 32 and its top extension 34, and the pull line 35 are molded as a one-piece body of suitable plastic, such as polypropylene or nylon.

OPERATION

In the use of this lancet, the user grasps the knob 39 and pulls line 35 to the position shown in full lines in FIG. 3 in which the bead 37 is immediately below the opening 36 in the bottom segment 13 of the frame. This retracts the holder 32 to the position in which the front face 34' of its top extension 34 engages the rearwardly-facing shoulder 30 on the rear top element 28 of the frame. As the spring arm 31 is being cocked, the inclined rear face 34" of the top extension 34 on the lancet blade holder 32 slides down over the inclined front face 29 of the front lip L on the cantilevered rear top element 28 of the frame, forcing the free front end of element 28 upward enough to let the holder extension 34 pass beneath it, after which the resiliency of the cantilevered element 28 causes it to spring back down to the position shown in FIG. 3. The nurse or other medical person now twists the pull line 35 by turning the knob 39 as shown in FIG. 7, causing the line to break at one of the grooves 40. This insures that the lancet can be used only once.

The patient's finger or thumb is pressed against the finger-engaging segment 15 on the front of the frame enough to push that segment, the front segment 14 and the cantilevered front top element 18 rearwardly to the position shown in FIG. 5. This front part of the frame pivots with respect to the bottom segment 13 about the reduced lower corner segment 14' as an axis. As the cantilevered front top element 18 of the frame moves rearward, its inclined rear face 20 slides downward and rearward across the inclined front face 29 of the cantilevered rear top element 28 of the frame, forcing the front end of element 28 up enough to disengage its shoulder 30 from the top extension 34 on the lancet blade holder 32. The holder 32 and its extension 34 now move rapidly forward beneath the front top element 18 of the frame under the impetus provided by the flexed spring arm 31. The lancet blade or needle 33 on the front end of the holder passes through the opening 17 in the finger-engaging segment 15 of the frame and penetrates the patient's finger or thumb, as shown in FIG. 5. The front end of holder 32 strikes the rear face of the finger-engaging element 15 to limit the depth of penetration of the lancet blade or needle 33 into the patient's finger. Also, the top extension 34 on the holder 32 wil engage the rearwardly facing shoulder 41 on the front part of the frame to limit the depth of penetration if the front of the holder 32 does not strike the back of finger-engaging segment 15 first.

The pull line 35 having been broken deliberately by twisting, as described, the spring arm 31 and holder 32 cannot be retracted again to permit another use of the lancet.

From the foregoing description it will be apparent that this lancet has an extremely simple construction which makes it easy to assemble and to use. Only the finger or thumb of the patient which is to be penetrated need be moved to trigger the automatic operation of the lancet. Proper positioning of this finger or the thumb on its seat on the housing of the lancet is assured because that finger or the thumb must be exerting pressure to release the spring arm from its retracted, cocked position.

I claim:

1. In an automatic surgical lancet comprising:
   a housing having a seat for receiving the tip of a patient's finger and an opening in said seat for passing a lancet blade;
   a spring arm inside said housing having a free end which is movable toward and away from said opening;
   a holding element for holding said spring arm cocked in a stressed position in which its free end is held away from said opening;
   a lancet blade holder on said free end of said spring arm;
   and a lancet blade carried by said holder;
   the improvement which comprises:
   a pull line attached to said holder and extending outside said housing to be pulled to a position for cocking said spring arm in said stressed position, said pull line having a weakened region near its attachment to said holder which is readily broken by twisting the pull line, whereby to prevent another cocking of said spring arm after the pull line is broken;
   said housing having an outer wall segment providing said seat which is inwardly displaceable by a push of the patient's finger against said seat;
   and means acting between said displaceable wall segment and said holding element to cause said holding element to release the spring arm from said cocked position for movement of its free end toward said opening when said displaceable wall segment is pushed inward.

2. In an automatic surgical lancet comprising:
   a housing having a seat for receiving the tip of a patient's finger and an opening in said seat for passing a lancet blade;
   a spring arm inside said housing having a free end which is movable toward and away from said opening;
   a lancet blade holder on the free end of said spring arm;
   a lancet blade carried by said holder;
   and a holding element for engagement with said holder to hold said spring arm cocked in a stressed position in which its free end is held away from said opening;
   the improvement wherein:
   said housing has an outer wall segment providing said seat which is displaceable inward by a push of the patient's finger against said seat;
   and further comprising:
   means acting between said displaceable outer wall segment of the housing and said holding element to cause said holding element to release said holder and permit movement of the spring arm from said cocked position toward said opening when said displaceable wall segment is pushed inward;
   and a pull line attached to said holder and extending outside said housing to be pulled to a position for cocking said spring arm in said stressed position, said pull line having a weakened region near its attachment to said holder which is readily broken by twisting the pull line, whereby to prevent another cocking of said spring arm after the pull line is broken.

3. In an automatic surgical lancet comprising:
   a housing having a seat for receiving the tip of a patient's finger and an opening in said seat for passing a lancet blade;
   a spring arm inside said housing having a free end which is movable toward and away from said opening;
   a lancet blade holder on the free end of said spring arm;
   a lancet blade carried by said holder;
   and a holding element for engagement with said holder to hold said spring arm cocked in a stressed position in which its free end is held away from said opening;
   the improvement wherein:
   said housing has an outer wall segment providing said seat which is displaceable inward by a push of the patient's finger against said seat;
   and further comprising:
   means acting between said displaceable outer wall segment of the housing and said holding element to cause said holding element to release said holder and permit movement of the spring arm from said cocked position toward said opening when said displaceable wall segment is pushed inward;
   said housing having a molded central frame piece of deformable and resilient plastic material which provides said spring arm, said displaceable outer wall segment of the housing, said holding element, and said means acting between said displaceable outer wall segment and said holding element;

said holding element being a flexible and resilient, elongated, cantilevered element extending toward said displaceable outer wall segment and presenting a free end which is engageable with said holder to hold said spring arm in its cocked position;

and said means acting between said displaceable outer wall segment and said holding element being a flexible and resilient, elongated arm having a cantilevered attachment to said displaceable outer wall segment and extending from its cantilevered attachment inward toward said free end of said holding element, said arm having a free end which is slidably engageable with said free end of said holding element to move said holding element out of engagement with the holder upon inward displacement of said displaceable outer wall segment;

and a pull line attached to said holder and extending outside said housing to be pulled to a position for cocking said spring arm in said stressed position, said pull line having a weakened region near its attachment to said holder which is readily broken by twisting the pull line, whereby to prevent another cocking of said spring arm after the pull line is broken.

4. An automatic surgical lancet comprising:

a housing having opposite side plates and a central frame engaged between said side plates, said central frame being a molded plastic body having;

a bottom segment;

a back segment extending up from said bottom segment at one end of the latter;

a rear top element having a cantilevered attachment to the upper end of said back segment and extending forward therefrom, said rear top element being flexible and resilient and terminating at its free front end in a depending lip which provides a rearwardly-facing shoulder, said lip presenting a downwardly and rearwardly inclined face on the front end of said rear top element;

a front segment extending up from said bottom segment at the opposite end of the latter, said front segment being joined to said bottom segment at a resilient corner of reduced cross-section to enable rearward pivoting of said front segment;

a finger-receiving segment attached to the upper end of said front segment and presenting a forwardly-facing concave seat with an opening therein for passing a lancet blade;

a front top element having a cantilevered attachment to said finger-receiving segment above said seat, said front top element extending rearward from its cantilevered attachment to said finger-receiving segment and terminating at its back end in a rearwardly and downwardly inclined face for sliding engagement with said inclined face on the front end of said rear top element;

a flexible and resilient spring arm extending up from said bottom segment behind said front segment and having a free upper end inside said housing;

a lancet blade holder on said free upper end of said spring arm, said holder having an upwardly-projecting extension with a forwardly-facing shoulder;

and a pull line extending from said holder down through said bottom segment, said pull line having a weakened region near its attachment to the holder;

and a lancet blade on the front end of said holder;

said pull line when pulled through said bottom segment retracting said holder to a position in which its upwardly-projecting extension engages behind said lip on the front end of said rear top element and said spring arm is cocked in a stressed position, said pull line being readily breakable in said weakened region by twisting the pull line after retracting said holder, whereby to prevent another cocking of said spring arm;

said front and finger-receiving segments being pivotable rearwardly about said corner between said front and bottom segments by the rearward force of a person's finger against said finger-receiving segment, thereby displacing said front top element rearwardly to slide its inclined back end face across said inclined front end face of said rear top element and force said depending lip on said rear top element upwardly to release said upwardly-projecting extension on said holder, permitting the upper end of said spring to move forward and force said lancet blade through said opening in said seat on the finger-receiving segment to penetrate the finger engaging said seat.

* * * * *